United States Patent [19]

Bogen

[11] Patent Number: 5,073,504
[45] Date of Patent: Dec. 17, 1991

[54] APPARATUS AND METHOD FOR IMMUNOHISTOCHEMICAL STAINING

[76] Inventor: Steven A. Bogen, 59 Millstone Rd., Readville, Mass. 02136

[21] Appl. No.: 459,747
[22] PCT Filed: Jul. 29, 1988
[86] PCT No.: PCT/US88/02605
§ 371 Date: Jan. 29, 1990
§ 102(e) Date: Jan. 29, 1990

[51] Int. Cl.$^5$ .............................. G01N 1/00; B01L 3/02
[52] U.S. Cl. ...................................... 436/174; 422/99; 422/100; 422/101
[58] Field of Search ................. 436/174; 422/99, 100, 422/101; 350/536, 535, 534; 206/387; 190/110

[56] References Cited

U.S. PATENT DOCUMENTS

| | | | |
|---|---|---|---|
| 2,628,694 | 2/1953 | Kushner | 190/109 |
| 2,631,632 | 3/1953 | Leachman | 190/109 |
| 2,942,520 | 6/1960 | Rose | 350/536 |
| 3,310,002 | 3/1967 | Wilburn . | |
| 3,503,665 | 3/1970 | Carter | 350/536 |
| 3,536,911 | 10/1970 | Grasenick et al. | 350/536 X |
| 3,768,914 | 10/1973 | Kinney et al. | 350/536 X |
| 3,802,842 | 4/1974 | Lange et al. | 422/57 X |
| 3,912,055 | 10/1975 | Malooly | 190/109 |
| 4,230,225 | 10/1980 | Okada et al. | 206/387 |
| 4,358,470 | 11/1982 | Rasmussen . | |
| 4,433,761 | 2/1984 | Winter et al. | 190/109 |
| 4,650,766 | 3/1987 | Harm et al. . | |
| 4,837,590 | 6/1989 | Sprague | 190/109 X |
| 4,846,970 | 7/1989 | Bertelsen et al. | 422/101 X |
| 4,847,208 | 7/1989 | Bogen | 436/174 |

FOREIGN PATENT DOCUMENTS 0201780 11/1986 European Pat. Off. ............ 350/536

*Primary Examiner*—Robert J. Warden
*Assistant Examiner*—Amalia L. Santiago
*Attorney, Agent, or Firm*—Hamilton, Brook, Smith & Reynolds

[57] ABSTRACT

A device and method for automating immunohistochemical staining of biological material on glass slides is presented. The slides are placed on the base with the tissue section facing upwards. A "chamber" consisting of a rectangular plastic box with a hinged overhead door is clamped directly over the tissue section. A rubber gasket seals the chamber—slide interface. Reagents are dropped on to the tissue section by means of the hinged overhead plastic door. When the door is closed, the chamber is sufficiently sealed so as to prevent evaporation. Washing of the tissue section is accomplished by the addition and aspiraton of buffer through ports in the chamber. The ports are connected via flexible tubing to a manifold. Because the wash steps are performed in tandem and do not require manual manipulation of slides, a significant time savings is realized. A mesh may be placed between reagents and the surface of the slide to spread a reagent over the surface of the slide.

41 Claims, 2 Drawing Sheets

APPARATUS AND METHOD FOR IMMUNOHISTOCHEMICAL STAINING

BACKGROUND

The present invention relates in general to apparatus and methods for applying reagents to and removing reagents from slides. In particular, the present invention relates to apparatus and methods for immunohistochemical staining of biological material on glass slides using economically small amounts of reagents.

Histology refers to the study of the microscopic structure of cells, tissues, and organs. The traditional method of analyzing the microscopic structure of an organ is to cut extremely thin sections of tissue on a special device called a microtome. After embedding the tissue in paraffin, a microtome can cut it 3-5 microns thick. Next, the section of tissue is attached to a glass slide. The thin tissue section is then stained with dyes or chemicals which are chosen for their ability to enhance various features in the tissue specimen.

Different dyes may be used to highlight different structures of cells or organs. For example, hematoxylin is a dye which stains cell nuclei purple, and eosin, often used in combination with hematoxylin, is a chemical compound which stains the cell cytoplasm red.

The staining process typically involves dipping the slides into small vats or jars containing the chemicals and/or dyes. Each vat or jar typically contains 0.2-2.0 liters.

More recently, a new type of staining process using specific antibody or DNA probes has been developed. These procedures have the advantage of high specificity and sensitivity, and are commonly used as an adjunct to traditional staining procedures. However, because the probes are far more expensive than dyes or stains, the probes are applied by a special technique which uses only several drops (about 50-200 microliters) of reagent.

In a common procedure for antibody-mediated staining ("immunohistochemistry"), frozen or paraffin-treated thin tissue sections (about 3-5 microns in thickness) are placed on glass slides. Frozen tissue sections are placed in acetone for temporary storage and are washed in buffered saline before use. Paraffin-treated tissue sections are baked at 56° C., deparaffinized in xylene, rehydrated in decreasing grades of ethanol and treated for 30 minutes with dilute hydrogen peroxide. The tissue sections are washed with buffered saline before use.

Next, each slide is blotted dry without disturbing the thin tissue section. Each slide is then placed in a humidified box, tissue side up. An appropriate first reagent is pipetted onto the tissue in a volume of 50-200 microliters. After the reagent has been added to each slide, the humidified chamber is closed, lest the reagent evaporate and leave the tissue dried and, therefore, spoiled.

After the appropriate incubation period (usually 30-60 minutes) each slide is removed from the humidified box and placed in a slide rack. The rack is immersed in buffered saline which is periodically replaced. After washing sufficiently to ensure that the first reagent is removed, each slide is manually removed from the saline, carefully dried and placed into the humidified chamber. A second reagent is then pipetted onto each slide and the slides are again incubated for 30 minutes. This procedure is repeated until all the incubation steps have been completed (usually 3-4 times).

A severe drawback of the present technique is that it is labor intensive. Steps which require individual manual handling of the slides (such as drying and transferring steps) are tedious and time consuming. Handling each slide at each incubation step (transferring a slide from the slide rack to the humidified box, drying the slide, and replacing the slide back in the rack) requires approximately one minute. For a typical run of 50 slides with four incubation steps each, this translates into 3.3 hours of technician time in addition to the time required for incubation and washing (about 45-75 minutes for each step).

An additional problem with the present technique is that a relatively large inequality of incubation time occurs when about 20 or more slides are stained. Because a significant amount of time is required to individually handle each slide, 15-20 minutes may elapse from the time the incubation of the first slide is begun until the incubation of last slide is initiated. Because the second to fourth incubation steps are typically only about 30 minutes in duration, a 50% disparity in incubation times results. This disparity diminishes the reliability of positive and negative control slides and makes comparisons between slides less valid.

In one approach to the control of the flow of fluid reagents, Thiers, U.S. Pat. No. 3,607,082 discloses a fluid-processing apparatus and a method for its use. In Thiers, metering and valving means charge a plurality of separate liquids into separate pipet chambers and discharge the liquids from the pipet chambers so that each succeeding liquid passes through the pipet chamber employed to receive the preceding liquid. A fluid receiving and transporting conduit has tractable wall portions adapted to receive the metered liquids from the pipets, means for forming movable seals in the conduit to isolate a metered quantity of liquid in a hydraulically isolated chamber, means for mixing the fluids in the chamber by compressing and releasing portions of the wall thereof, processing means for performing various unit processes on the fluid mixture in a given chamber and discharge means for removing fluid mixture from the conduit. A branched-arm valve, fitted with means for selectively closing arms thereof is employed as a valving means in charging and dispensing fluids into and from the pipet chambers. The system is described for use in carrying out various processes of chemistry, microbiology or the like. However, Thiers does not disclose a solution to the problems of applying a small amount of expensive reagent to and removing the reagent from a slide.

Reunanen, U.S. Pat. No. 3,754,863, discloses a method and apparatus for dosing reagents and for incubating and sampling a reaction mixture. In the method, reagents are drawn into reaction syringes in which an incubation is carried out and from which samples are discharged in one or more portions. The apparatus consists of a syringe unit, reaction syringes mounted on a single frame, syringes containing stopping liquid and an internal standard. Vessels for the reagents, instruments for feeding reagents and for the automatic adjustment of pistons and for transferring absorption plates, and a thermostat are mounted on a fixed outer frame. The invention is indicated to be particularly useful for macromolecular investigation of radioactive parent substances where the sample is absorbed into a porous medium and where it is washed automatically. Nevertheless, Reunanen does not disclose methods or apparatus particularly suited to manipulation of small amounts of reagent materials for application to tissue sections of the sort which are employed in immunohistochemistry.

In another approach, Wallach, U.S. Pat. No. 3,764,215, discloses a medical specimen, such as a Pap smear, blood or bacteria sample, placed on a thin transparent flexible slide. Several slides are affixed to one another or to an elongated flexible carrier and then wound on a reel. A plurality of such reels are loaded on top of one another into a vertical processing tank which is filled sequentially with chemicals and stains as required. Subsequently, the reel is removed from the tank and the slides are microscopically screened to detect diseases such as cancer and the like. However, the expense of immunohistochemical reagents and the degree of care with which they must be applied render impractical the dipping of reels of slides into tanks of reagent.

In Becker et al., U.S. Pat. No. 3,837,795, a method for staining biological material on flat slides is disclosed. A group of slides is successively dipped into vessels containing different liquids conventionally used in staining. The time a group of slides is in any given vessel is controlled in accordance with the staining technique desired. One of the vessels has a de-colorizing agent in it. In this last vessel, a laminar flow of de-colorizing liquid is directed over the flat faces of the slides to create a chimney effect which minimizes cross-contamination. The de-colorizing liquid is withdrawn continuously from its vessel, filtered and re-introduced into the vessel. However, because Becker et al. teaches the dipping of slides into vessels, the approach of Becker et al. suffers from the disadvantages common to techniques where large quantities of reagent are employed.

Hastka, European Patent Publication No. 201,780, described an apparatus for histological examination which has a plurality of chambers, each chamber having wall delineating apertures and having a system of a magnet and a magnetically attracted material to hold each chamber to a slide. Each chamber is said to have an outlet conduit with a valve connected to it, and these outlet conduits are reported to be connected by a vacuum source by way of a manifold. Rasmussen, U.S. Pat. No. 4,358,478, describes a closed chamber with an inlet and an outlet port, the inlet port being connected to a valve through which fluid from a reservoir is reported to be fed. However, Hastka does not suggest an inlet port for applying materials to a chamber reversibly sealed to the surface of a slide, and although Rasmussen discloses an inlet port, it is a port to a chamber which is not reversibly sealed to the surface of a slide. Therefore, neither Rasmussen nor Hastka suggests an apparatus or method to provide histological slide-staining chambers with a controllable flow of reagent or rinsing solution for the treatment of biological samples on slides in a fashion useful for reproducible staining of large numbers of slides.

Cytochemistry apparatus is disclosed in Brigati, a presentation made at the Massachusetts Society for Histotechnology 13th Annual Seminar, Apr. 23-25, 1987, in Eastham, Mass. A similar but less detailed presentation was made at the Spring Meeting of the American Society of Clinical Pathologists, Mar. 28-Apr. 2, 1987, San Francisco, Calif. Brigati discloses an apparatus for immunocytochemistry which employs a capillary gap to facilitate application and removal of small amounts of reagents. Specifically, a glass slide with a protruding spacer shim is closely opposed to a slide to which a thin tissue sample is attached, thus forming a capillary gap between the slides. The gap between the opposed slides is alternately passed over reagent-filled recesses in a hydrophobic surface or over a blotter to respectively introduce or remove a reagent. Nevertheless, the reliance upon capillary action to properly distribute reagent to the surface of a tissue sample may affect the uniformity of distribution (e.g. due to the formation of bubbles in the capillary space) and limits the thickness of tissue samples which may be used. Moreover, special slides having a painted spacing shim are required. Another disadvantage of this technique is that the tissue section must be applied to the slide near the bottom end. If the tissue is too far up, the reagent may not climb sufficiently by capillary action to immerse the tissue section.

Therefore, there is still a need for an efficient and rapid yet simple apparatus for immunohisto-chemical staining.

SUMMARY OF THE INVENTION

Accordingly, the present invention provides apparatus for the application and removal of materials to a slide including a plurality of chambers each having at least one wall delimiting a first aperture and a second aperture. The present invention also provides means for sealing the wall about each of the first aperture to a surface of a slide, an inlet port passing through the wall, an outlet port passing through the wall, a door rotatably opposable to the second aperture, a first valve coupled to the inlet port of each of the chambers, a second valve coupled to the outlet port of each of the chambers, a reservoir coupled to the first valve, a source of suction coupled to the second valve, a first manifold having an inlet and a plurality of outlets, an outlet of the first manifold being coupled to said inlet port of each of said chambers, and the inlet of the first manifold being coupled to said reservoir, and a second manifold having an outlet and a plurality of inlets, an inlet of the second manifold being coupled to the outlet port of each of the chambers, and the outlet of said second manifold being coupled to the source of suction.

Apparatus according to the present invention also provides a pipette and a third valve coupled between the pipette and the source of suction.

According to the present invention, the means for sealing preferably comprises a surface, the chambers being rotatably affixed to the surface, and a gasket around the circumference of the first aperture and between each of the chambers and the surface.

In a method according to the present invention, a portion of a surface of a slide is sealed, preferably with a gasket, to an aperture in a chamber having an inlet port and an outlet port, each port being formed by a fluid conduit passing through a wall of the chamber. Material is applied to portion of the surface of the slide by flushing with material passed through the inlet port. Material is removed from the surface of the slide by aspirating at least some of the material through the outlet port, which port is at least indirectly connected to a source of suction.

It is an object of the present invention to significantly reduce the amount of individual manipulation of slides required in procedures where minimal quantities of reagent are used, such as in immunohistochemistry and in situ DNA hybridization.

It is another object of the present invention to provide means by which tandem access is provided to biological material on slides while retaining the flexibility of individual access if desired for the administration and removal of buffer and reagents.

A further object of the present invention is to provide means for incubating biological material on slides in the presence of small amounts of reagent, on the order of several drops.

Another object of the present invention is to increase the number of slides which may be processed in one run.

It is yet another object of the present invention to decrease the disparity in incubation time which results from sequential handling of slides.

A further object of the present invention is to eliminate the need for a large humidified box to contain slides during application of reagents.

An apparatus according to the present invention for the application of materials to a surface of a slide includes a mesh located between the materials and the surface. The mesh preferably has a spacing between fibers of 50-1500 microns and most preferably has a spacing of 50-300 microns.

A method for the application of materials to a slide includes the steps of positioning a mesh between the materials and the slide and applying the materials to the slide through the mesh.

Slide chambers according to the present invention may be radially disposed on a rotating carousel, which carousel may be located beneath a reagent dispenser holder so that a slide in the slide carousel may be indexed to a position beneath a position of a reagent dispenser to be applied to the slide from the reagent dispenser.

DETAILED DESCRIPTION

Devices according to the present invention are useful for the automatic washing and drying of slides during immunohistochemical staining. Such devices are also suitable for other slide staining techniques where small quantities of reagent are used, including DNA in situ hybridization and enzyme histochemistry.

"Washing" a slide refers to rinsing a reagent from a slide by an excess of buffer. Buffer is added and then aspirated to thereby remove reagent applied to tissue section. A washing step is normally important between reaction steps.

In a device according to the present invention, washing is accomplished by first opening a valve which is placed between a buffer reservoir (e.g., a flask filled with buffer) and a manifold. The manifold in turn feeds one or more slide chambers. When the chambers are one half to three-quarters full of buffer, the valve controlling buffer flow (the "buffer valve") is closed. A second valve placed between a suction source and a second manifold is then opened. This second manifold is also connected via flexible tubing to one or more slide chambers. By opening this second valve (hereinafter referred to as a "suction valve"), the buffer is aspirated from all slide chambers.

By repeating the process of addition to and aspiration of buffer from a slide chamber 4-5 times, a reagent is completely removed. This technique of washing slides in tandem is more rapid than the current technique. Moreover, no drying of slides with a paper cloth is required to remove excess buffer. The suction performs this task automatically.

In addition to a main suction pathway, an accessory suction valve (normally closed) may be used to channel the suction force exclusively to a single pipette, if desired. The accessory suction pathway is useful to individually aspirate slide chambers, if desired.

Figure 1:
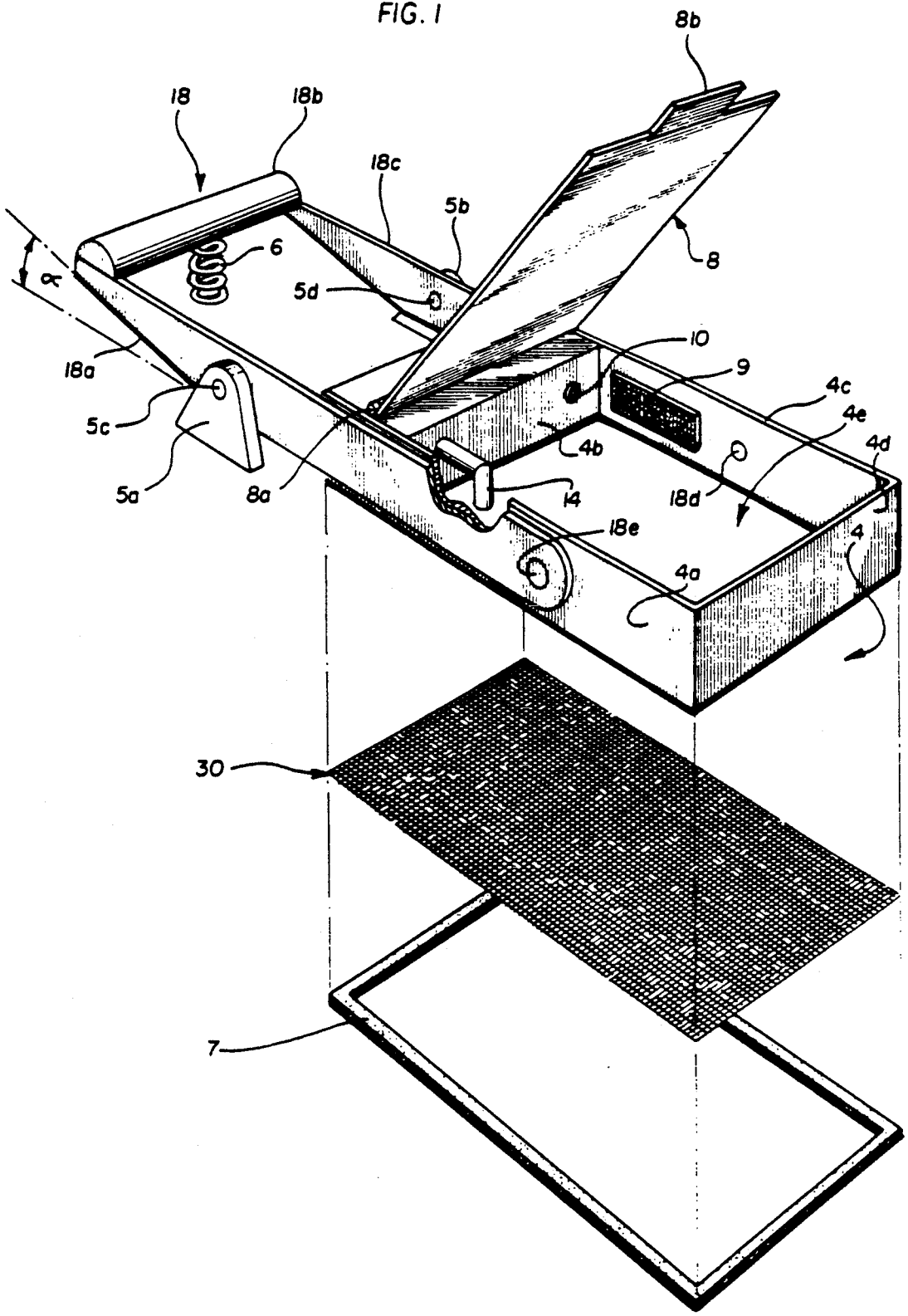
FIG. 1 is a perspective view of a slide chamber according to the present invention.

As illustrated in FIG. 1, a slide chamber 4 according to the present invention has four rectangular sides 4a, 4b, 4c and 4d, which sides are joined at right angles to form a box-shaped chamber 4e having a superior and an inferior aperture. A gasket 7 is affixed to an edge of each of sides 4a, 4b, 4c and 4d, which edges delimit the inferior aperture. Although gasket 7 is depicted in FIG. 1 as being separated from slide chamber 4 by a mesh 30, it is intended that mesh 30 contact the surface of a slide in a preferred embodiment. The superior aperture is formed by edges of sides 4a, 4b, 4c and 4d which lie directly opposite those which delimit the inferior aperture. A rectangular plastic door 8 has one edge which is attached to a hinge 8a affixed to one end of one edge of side 4b. A second hinge (8c) is not shown. In a first "closed" position, door 8 is virtually coextensive with the superior aperture, and thus capable of enclosing chamber 4 on a fifth side. Rotation of door 8 on hinges 8a and 8c into any other position provides access to the interior of chamber 4. An edge of door 8 opposite hinge 8a may have a lip 8b to facilitate manual rotation of door 8 on hinges 8a and 8c.

A lever assembly 18 has a first arm 18a, a second arm 18c and a crosspiece 18b. A first end of arm 18a is attached at a right angle to a first end of crosspiece 18b and, directly opposite arm 18a, a first end of arm 18c is attached at a right angle to a second end of crosspiece 18b. A medial portion of arm 18a is rotatably attached to a mount 5a by a pin 5c, and mount 5a is affixed to a flat surface 1. A medial portion of arm 18c is rotatably attached to a mount 5b by a pin 5d directly opposite the attachment of arm 18a to pin 5c, and mount 5b is affixed to a flat surface 1. Between pin 5c and crosspiece 18b, arm 18a diverges from surface 1 at an an angle α, while distal to pin 5c and crosspiece 18b, arm 18a is parallel to surface 1 up to the end of arm 18a which is rotatably attached to side 4a by a pin 18e. Between pin 5d and crosspiece 18b, arm 18c diverges from surface 1 at an an angle α, while distal to pin 5d and crosspiece 18b, arm 18c is parallel to surface 1 up to the end of arm 18a which is rotatably attached to side 4a by a pin 18d. A spring 6 is affixed at a first end to surface 1 and at a second end to crosspiece 18b.

A tubular suction port 14 passes through side 4b along a normal line to side 4b. A first end of port 14 lies outside chamber 4 while a second end of port 14 bends within chamber 4 to terminate in an opening at a distance D (preferably 1/64 to 1/128 inch) from surface 1. A tubular inlet port 10 passes through side 4b along a normal line to side 4b. A first end of port 10 lies outside chamber 4 while a second end of port 10 ends within chamber 4. A gauze strip 9 is affixed to side 4c.

In use, crosspiece 18b is depressed against spring 6 to lift chamber 4. A slide is positioned on surface 1 so that a tissue section to be treated lies within the inferior aperture of chamber 4. Then cross-piece 18b is released so that gasket 7 is pressed by the action of spring 6 as transmitted along arms 18a and 18c against the surface of the slide to seal the tissue sample within chamber 4.

Figure 2:
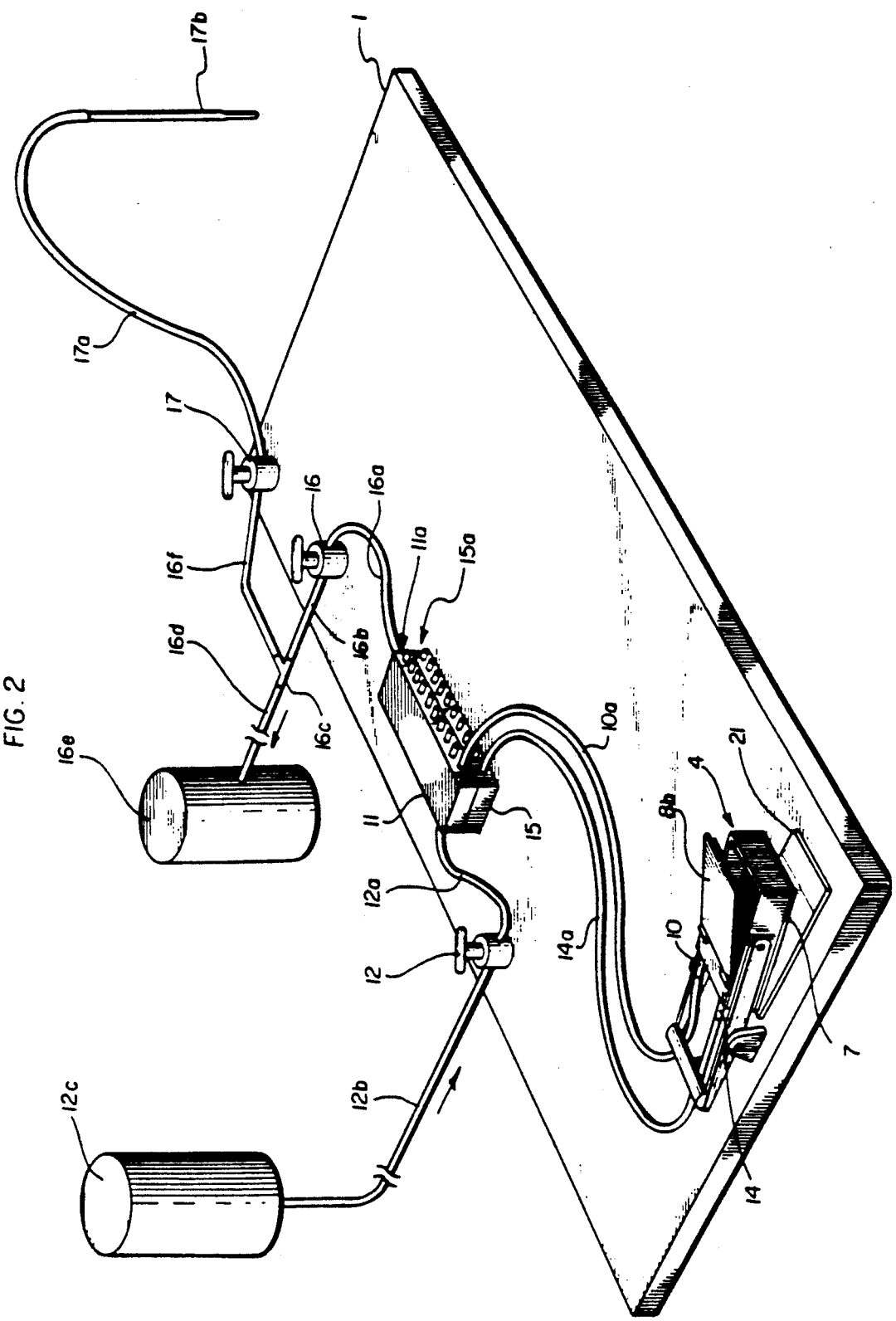
FIG. 2 is a perspective view of buffer and suction apparatus employed in association with the chamber of FIG. 1 according to the present invention.

By lifting hinged plastic door 8 in the top of chamber 4, a first reagent may be dropped on the tissue section, and the door may be closed to prevent evaporation. The slide chamber 4 also serves to prevent a reagent from spilling off the edge of the side. Because the chamber 4 is sealed to a slide 21 by compressing a rubber gasket 7 against a surface of slide 21 (as shown in FIG. 2), the drops of reagent must remain in the area delimited by the boundaries of the chamber 4. Thin piece of gauze 9 may be attached to the inside aspect of the slide chamber and wetted to further humidify the air within the slide chamber. Gauze 9 may be wetted with water or buffer. In practice, the gauze becomes soaked with buffer during each wash cycle as buffer fills the chamber when a "buffer valve" is open.

After the appropriate incubation period determined by known parameters of the histochemical procedure being performed, (usually 30-60 minutes), the first step reagent is removed by first adding and then aspirating buffer from the slide chamber 4.

A flexible mesh 30 may be placed within the inferior aperture of the slide chamber. The mesh permits reagents and buffers to pass through and also acts as a "wick". The mesh has a higher affinity for water than glass and therefore guides the water-based reagent along the glass surface. Surface tension is overcome, ensuring an even and smooth distribution of reagent. A suitable mesh is a polyester monofilament mesh,. 260 micron spacing, as 7-260/41 sold by TETKO Inc., Elmsford, N.Y. Such a mesh is commonly used in silk screening and may be purchased from an art supply store. Other potentially useful materials are preferably materials which are hydrophilic and those which exhibit a wicking action and which include porous filter paper, polyethylene, polypropylene, nylon, Teflon ®, Fluortex ® and metal.

The spacing of the mesh fibers may not be critical. Extremely fine meshes (less than approximately 25 microns spacing) may not be suitable because the reagent is difficult to remove by washing (the small spacing may inhibit fluid flow across the mesh). Moreover, the optimal spacing appears to depend on the material. Nylon meshes may work well at much wider spacing up to about 1500 microns.

Brigati, a presentation made at the Massachusetts Society for Histotechnology 13th Annual Seminar, Apr. 23-25, 1987, in Eastham, Mass., Ormanns et al., *Histochemistry*, 72, 315-19 (1981) and Miller, U.S. Pat. No. 4,607,921 entail two solid flat surfaces apposed to one another, separated by a spacer to create a narrow gap. Reagent and buffer are added to an edge of a slide (i.e., to the opening of the gap).

The problem of overcoming surface tension in the capillary gap approach of Brigati may be addressed by adding a non-ionic detergent to the washing buffer. A disadvantage to the use of detergent is that it adds another variable to the reaction, i.e. the detergent must be titrated to ensure that enough is present for proper reagent spreading but not so much that it inhibits the tissue-reagent reaction.

The embodiment of the present invention which employs a flexible mesh does not create a capillary type gap and therefore does not require a spacer element and does not depend on capillary action to spread the drop. The mesh may be applied directly to the slide underneath the slide chamber. The tissue section is not damaged because of the soft texture of the mesh. The reagent and buffer are applied to the broad aspect of the slide rather than the edge. This latter feature is advantageous for the automation of reagent aliquoting.

The mesh may be secured to the inferior aperture by either an adhesive or by folding the edges up against an outside wall of the slide chamber and securing the mesh with a clamp running around the circumference of the aperture of the chamber. A gasket for sealing the chamber-slide interface may be placed outside the chamber wall rather than underneath it in embodiments employing mesh 30.

Without the mesh drop spreader 30, the reagent spreads well if the area around the tissue secton is kept moist. Moisture may be maintained around the tissue secton by drying each slide through an accessory suction pipette. The area around the tissue may be dried with the pipette without drying the tissue itself. For further automation, however, such individualized attention is not feasible.

A further advantage to the use of mesh 30 is that smaller volumes of reagent may be used. Reagents are usually expensive because they include antibody or DNA. Because the drop spreader causes an even but thin layer of reagent to spread over the slide, less reagent is required to cover a given area. In preliminary experiments, reagent usage may be cut by half to two thirds.

Such drop spreading mesh may be used in other apparatus relating to slides. For example, the mesh may be used directly (without a slide chamber) and the washing and incubation steps may be performed in one common incubation chamber.

As illustrated in FIG. 2, the first end of inlet port 10 is connected to a first end of tubing 10a, a second end of which is connected to one of a plurality of output nipples 11a of a buffer manifold 11. An input nipple (not shown) of manifold 11 is connected to a first end of tubing 12a, a second end of which is connected to a buffer valve 12. Valve 12 is also connected to a first end of tubing 12b, a second end of which is connected to a buffer reservoir 12c.

As also illustrated in FIG. 2, the first end of suction port 14 is connected to a first end of tubing 14a, a second end of which is connected to one of a plurality of input nipples 15a of a suction manifold 15. An output nipple (not shown) of manifold 15 is connected to a first end of tubing 16a, a second end of which is connected to a first suction valve 16. Valve 16 is also connected to a first end of tubing 16b, a second end of which is connected to a first input of Y-connector 16c. A second input of Y-connector 16c is connected to a first end of tubing 16f, a second end of which is connected to a second suction valve 17. Suction valve 17 is also connected to a first end of tubing 17 a, a second end of which is connected to a wide end of a pipette 17b. An output of Y-tube 16c is connected to a first end of tubing 16d, a second end of which is connected to a source of suction 16e.

Cut sections of acrylic plastic may be used to construct chamber 4 and manifolds 11 and 15. Chamber 4 may be of any convenient shape, including round and square. Manifolds 11 and 15 may be created by drilling fluid pathways from within a solid acrylic block. Attachments for tubing (nipples 11a and 15a) may be short segments of brass tubing which are press-fit into the acrylic block.

Chamber 4 may be constructed by individually cutting each wall and then gluing the walls together by methods well known to those skilled in the art. Holes for pins may be drilled in advance. All pieces relating to the lever mechanism may be also individually cut from acrylic and glued. Ports 10 and 14 may be pieces of brass tubing glued in place. A 90 degree bend in port 14 may be made by welding two pieces of brass tubing together. Valves 12, 16 and 17 may be polypropylene stopcocks available as polypropylene Nalgene ® stopcocks from Consolidated Plastics, Macedonia, Ohio. Also available from Consolidated Plastics are Y-connectors usable as Y-connector 16c as Nalgene ® polypropylene connectors; tubing usable for tubing 10a, 12a, 12b, 14a, 16a, 16d, 16f and 17a as Tygon ® flexible tubing; and acrylic sheet useful for construction of chamber 4 as Lucite ® S-A-R acrylic sheet.

Buffer flow is started by opening fluid valve (designated "buffer valve") 12 connected between the manifold inlet nipple and a buffer reservoir 12c. When the slide chamber is approximately ½-¾ full with buffer, valve 12 is closed.

The buffer is then aspirated from the slide chambers through an opening of a suction port 14. The suction port is similar to the buffer inlet port 10 except that it has an opening situated approximately 1/64 of an inch above the surface of a glass slide 22. This allows all of the buffer to be aspirated until less than 1/64" layer of buffer remains on the slide 22. Suction port consists of ⅛ inch brass tubing with a 90 degree bend. The open end is very close to the slide (approximately 1/64-1/128 of an inch away), so that all excess buffer within each slide chamber is aspirated after each wash step. In practice and with a strong suction source, virtually all of the buffer is aspirated.

Suction pathways are similar in configuration to those used for the buffer. Namely, the suction port is connected to a manifold 15 which is connected to a suction source via a valve 16 designated the "suction valve". When the buffer is fully aspirated, suction valve 16 is closed.

An alternate suction pathway is also provided via a separate valve 17. This pathway allows the suction force to be diverted through flexible tubing to a disposable Pasteur pippette, allowing the user to individually aspirate any chamber.

Slides may be washed with buffer by alternately opening and closing valves 12 and 16 so that buffer is added and then aspirated from the incubation chambers 4. Approximately 3-5 cycles are necessary for complete removal of any reagent, requiring less than 30 seconds. If small drops of buffer remain in the corners of an incubation chamber, it can be directly aspirated via the Pasteur pippette/alternate suction pathway.

A second reagent may be added in the same manner as the first and the entire process repeated until all reagents have been applied. At the end, the slide is removed and cover-slipped.

Although the present invention has been described in terms of a preferred embodiment, it is understood that modifications and improvements will occur to those skilled in the art upon consideration of the present invention. For example, although a single slide chamber 4 is described herein, it is understood that a plurality of slide chambers may be connected by way of manifolds 11 and 15. Unused nipples on manifolds 11 and 15 may, of course, be capped to prevent leakage. Moreover, although the placement of valves 12, 16 and 17 on a side of each of manifolds 11 and 15 opposite chamber 4 is preferred, the use of valves within the manifolds or on the chamber side of the manifolds is within the scope of the present invention.

Furthermore, chamber 4 may be injection-molded, the brass tubing for the ports 10 and 14 being replaced with injection-molded plastic structures which are part of wall 4b. This eliminates the need to cut and weld brass pieces of tubing. The number of chambers per board may be also increased. The Y-shaped connector 16c and valves 16 and 17 may be replaced with a 3-way valve. All hinged aspects of the chamber may be injection molded so that plastic round tabs form pivots for hinges which allow hinged aspects 5c/5d, 18a/18b, 18d/18e to be snapped into place. In addition, other types of valve, including solenoid- controlled valves permitting electrical control of valve opening and closing.

Although the reservoir described herein is described as a buffer reservoir, other reagents than buffers may be similarly introduced into chamber 4 according to the present invention by coupling to manifold 11 or additional manifolds. As used herein, coupling is not limited to direct connection but includes connection through additional elements, for example, additional valves, which permit a fluid to pass between the "coupled" elements.

In addition, although chamber 4 is described as a rectangular box herein, a cylindrical or any useful other shape may be employed to contain fluids applied to slide 21 consistent with the present invention.

Slide chambers according to the present invention may be mounted in a radial pattern around a central axle. Rotatable couplings for suction and buffer may exist within an axle for connection to the manifolds. A console may be located in the front facing an operator. An "advance" button may rotate the carousel clockwise; a "reverse" button may rotate the carousel counter-clockwise.

The slide chambers may not have an attached hinged cover. Instead, the chambers may be sealed from above with a common cover shaped like a ring when viewed from above. The cover may be moved up or down by a solenoid to seal the upper aperture of each slide chamber. A button on the console provides for control of the position of the cover.

The cover may not extend over the "index position"—the position on the carousel at the front, center. During incubation, therefore, no slide chamber may be present at the index position. The following features may be present at the index position. An inverted lens may be used for viewing the slide. A single 10× objective lens may be used with a provision for some (preferably about 12-15) mm lateral mobility.

A detachable array of precision pumps may be employed for precise addition of fluid reagent through microbore flexible tubing to the index position of a carousel slide chamber. By using 1 mm outer diameter tubing (which may be Mini Teflon ® TFE tubing), 15-20 different segments of tubing may be placed in a detachable harness and positioned directly over the central portion of the slide. These tubing segments may be connected directly to the precision pumps for precise addition of microliter quantities of the desired reagents.

An alternative arrangement, eliminating the need for microbore tubing, includes a small detachable rotating carousel of precision repeating reagent dispensers (e.g. syringe pumps) placed above the index position. Only one reagent dispenser is directly above the slide chamber in the index position at any one time. A reagent dispenser holder moves (e.g. laterally or by rotation) until the desired reagent is above the slide chamber and automatically dispensed in microliter quantities.

As an alternative to a rotating reagent carousel (i.e. a reagent carousel) which rotates to place a desired reagent above an index position, a movable reagent dispenser holder may have a mechanism for lateral motion and a robotic arm or X-Y indexing apparatus may be employed to apply materials to slides.

After staining is complete, an entire reagent dispenser holder may be detached and placed in a refrigerator for storage. A combination of designs may also be used— e.g. a reagent dispenser for first stage reagents and a microbore tubing feeding arrangement for second and third stage reagents or for chromogen. Dispensers may be stacked to increase capacity. The reagent dispenser may thus be a feature useful for labs with high antibody diversity requirements.

Reagents may also be manually added to a chamber from a dropper bottle or pipette.

As an alternative to the mesh drop spreader described above, an atomizer may spray a fine mist or moisture on a biological sample to ensure an even spread of drop(s) of reagent over the sample. By the current technique of immunohistochemical slide staining, a small amount of moisture is also left on the tissue specimen.

An accessory suction pipette may be lowered to the slide surface to aspirate the liquid contents of the slide chamber. An overhead lamp may be provided for illumination. A solenoid actuator for depressing the slide chamber lever may be used to raise and lower the slide chamber for slide insertion and removal.

In addition, for cytology applications, a separation wall may divide the chamber into compartments above the slide.

Accordingly, it is intended that all such modifications and improvements come within the scope of the invention as described.

I claim:

1. Apparatus for the application of a solution to and removal of the solution from a slide comprising:
    a supporting surface which is capable of providing mechanical support to a slide;
    a transparent slide on the supporting surface, the slide carrying a specimen;
    a chamber having a wall delimiting a first aperture, said chamber being attached to said supporting surface; and
    means for apposing said chamber to a surface of said transparent slide without disengaging said chamber from said supporting surface and for moving said chamber from the surface of said transparent slide without disengaging said chamber from said supporting surface.

2. The apparatus as recited in claim 1 further comprising a port in said wall.

3. The apparatus as recited in claim 1 wherein said wall delimits a second aperture and wherein said chamber further comprises a door mounted to permit application of said door to close said second aperture.

4. The apparatus as recited in claim 1 further comprising a water absorbent material in said chamber for humidifying the air within the chamber.

5. The apparatus as recited in claim 1 further comprising a plurality of said chambers affixed to said supporting surface.

6. The apparatus as recited in claim 5 further comprising a distribution manifold and a first means for coupling between a port in said wall of each of said chambers and said distribution manifold.

7. The apparatus as recited in claim 6 further comprising second means for coupling and a valve coupled by said second means for coupling to said distribution manifold.

8. The apparatus as recited in claim 7 further comprising third means for coupling and a suction source coupled to said valve by third means for coupling.

9. The apparatus as recited in claim 7 further comprising fourth means for coupling and a liquid container coupled to said valve by said fourth means for coupling.

10. The apparatus as recited in claim 1 further comprising:
    a source of suction;
    a pipette;
    means for coupling; and
    a valve coupled by said means for coupling between said pipette and a source of suction.

11. Apparatus for the application of a solution to and removal of a solution from a slide comprising:
    a transparent slide carrying a specimen;
    a chamber having a wall delimiting a first aperture;
    means for apposing said first aperture to a surface of said transparent slide and for lifting said chamber from said transparent slide; and
    means for applying pressure to said chamber and said transparent slide and for maintaining the chamber and transparent slide in apposition.

12. The apparatus as recited in claim 11 further comprising a port in said wall.

13. The apparatus as recited in claim 11 wherein said wall delimits a second aperture and wherein said chamber further comprises a door mounted to permit application of said door to close said second aperture.

14. The apparatus as recited in claim 11 further comprising a water absorbent material in said chamber for humidifying the air within the chamber.

15. The apparatus as recited in claim 11 further comprising a plurality of said chambers.

16. The apparatus as recited in claim 15 further comprising a distribution manifold and first means for coupling between a port in said wall in each of said chambers and said distribution manifold.

17. The apparatus as recited in claim 16 further comprising second means for coupling and a valve coupled by said second means for coupling to said distribution manifold.

18. The apparatus as recited in claim 17 further comprising third means for coupling and a suction source coupled to said valve by third means for coupling.

19. The apparatus as recited in claim 17 further comprising fourth means for coupling and a liquid container coupled to said valve by said fourth means for coupling.

20. The apparatus as recited in claim 11 further comprising:
    a source of suction;
    a pipette;
    means for coupling; and
    a valve coupled by said means for coupling between said pipette and a source of suction.

21. Apparatus for the application of a solution to and removal of a solution from a slide comprising:
    a surface;
    a transparent slide on the surface, the transparent slide carrying a specimen;

a mount attached to said surface;

a chamber having a wall delimiting a first aperture, said chamber being rotatably attached to said mount;

means for apposing said first aperture to a surface of the transparent slide and for moving said chamber from said surface of the transparent slide.

22. The apparatus as recited in claim 21 further comprising a port in said wall.

23. The apparatus as recited in claim 21 wherein said wall delimits a second aperture and wherein said chamber further comprises a door mounted to permit application of said door to close said second aperture.

24. The apparatus as recited in claim 21 further comprising a water absorbent material in said chamber for humidifying the air within the chamber.

25. The apparatus as recited in claim 21 further comprising a plurality of said chambers.

26. The apparatus as recited in claim 25 further comprising a distribution manifold and first means for coupling between a port in said wall of each of said chambers and said distribution manifold.

27. The apparatus as recited in claim 26 further comprising second means for coupling and a valve coupled by said second means for coupling to said distribution manifold.

28. The apparatus as recited in claim 27 further comprising third means for coupling and a suction source coupled to said valve by third means for coupling.

29. The apparatus as recited in claim 27 further comprising fourth means for coupling and a liquid container coupled to said valve by said fourth means for coupling.

30. The apparatus as recited in claim 21 further comprising:
 a source of suction;
 a pipette;
 means for coupling; and
 a valve coupled by said means for coupling between said pipette and a source of suction.

31. Apparatus for the application of a solution to and removal of a solution from a slide comprising:
 a transparent slide carrying a specimen;
 a rotatably hinged chamber having a wall delimiting a first aperture;
 means for apposing said first aperture to a surface of said transparent slide and for moving said chamber from said surface of said transparent slide.

32. The apparatus as recited in claim 31 further comprising a port in said wall.

33. The apparatus as recited in claim 31 wherein said wall delimits a second aperture and wherein said chamber further comprises a door mounted to permit application of aid door to close said second aperture.

34. The apparatus as recited in claim 31 further comprising a water absorbent material in said chamber for humidifying the air within the chamber.

35. The apparatus as recited in claim 31 further comprising a plurality of said chambers.

36. The apparatus as recited in claim 35 further comprising a distribution manifold and first means for coupling between a port in said wall of each of said chambers and said distribution manifold.

37. The apparatus as recited in claim 36 further comprising second means for coupling and a valve coupled by said second means for coupling to said distribution manifold.

38. The apparatus as recited in claim 37 further comprising third means for coupling and a suction source coupled to said valve by third means for coupling.

39. The apparatus as recited in claim 37 further comprising fourth means for coupling and a liquid container coupled to said valve by said fourth means for coupling.

40. The apparatus as recited in claim 31 further comprising:
 a source of suction;
 a pipette;
 means for coupling; and
 a valve coupled by said means for coupling between said pipette and a source of suction.

41. A method for the application of a fluid to and removal of a fluid from a slide comprising the steps of:
 providing an impermeable slide carrying a specimen;
 apposing an aperture of a chamber to a portion of the impermeable slide;
 adding a liquid to said portion of the impermeable slide;
 aspirating liquid from the portion of the impermeable slide; and
 removing the aperture from the slide.

* * * * *